(12) United States Patent
Warner et al.

(10) Patent No.: US 8,612,254 B2
(45) Date of Patent: *Dec. 17, 2013

(54) SYSTEM AND METHOD TO MANAGE A QUALITY OF DELIVERY OF HEALTHCARE

(75) Inventors: Adrian Warner, Delafield, WI (US); Crispian Sievenpiper, Waukesha, WI (US); Jeffrey Solliday-McRoy, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/461,524

(22) Filed: May 1, 2012

(65) Prior Publication Data

US 2012/0215556 A1 Aug. 23, 2012

Related U.S. Application Data

(63) Continuation of application No. 12/241,193, filed on Sep. 30, 2008, now Pat. No. 8,190,450.

(51) Int. Cl.
    *G06Q 50/22* (2012.01)
(52) U.S. Cl.
    USPC .................................. 705/2; 600/300; 705/3
(58) Field of Classification Search
    USPC ........................................ 600/300; 705/2, 3
    See application file for complete search history.

(56) References Cited

U.S. PATENT DOCUMENTS

| | | | |
|---|---|---|---|
| 5,887,133 A | | 3/1999 | Brown et al. |
| 5,935,060 A * | | 8/1999 | Iliff ............................. 600/300 |
| 7,156,808 B2 * | | 1/2007 | Quy ............................. 600/300 |
| 7,555,436 B2 * | | 6/2009 | Brown ............................. 705/2 |
| 8,190,450 B2 | | 5/2012 | Warner et al. |
| 8,407,063 B2 * | | 3/2013 | Brown ............................. 705/2 |
| 8,419,636 B2 * | | 4/2013 | Brown ......................... 600/300 |
| 8,463,623 B2 * | | 6/2013 | Ware et al. ....................... 705/3 |
| 8,489,428 B2 * | | 7/2013 | Brown ............................. 705/3 |
| 2005/0102159 A1 | | 5/2005 | Mondshine |
| 2007/0214007 A1 * | | 9/2007 | Hackner .......................... 705/2 |
| 2010/0082363 A1 | | 4/2010 | Warner et al. |

OTHER PUBLICATIONS

United States Patent and Trademark Office, "Non-Final Rejection," issued in connection with U.S. Appl. No. 12/241,193, mailed on Nov. 10, 2010, 14 pages.

United States Patent and Trademark Office, "Final Rejection," issued in connection with U.S. Appl. No. 12/241,193, mailed on Jul. 12, 2011, 14 pages.

(Continued)

*Primary Examiner* — Lena Najarian
*Assistant Examiner* — Teresa Woods
(74) *Attorney, Agent, or Firm* — Hanley, Flight and Zimmerman, LLC

(57) ABSTRACT

A system and method to manage a quality of delivery of healthcare to a patient. The method includes tracking completion of a portion of a protocol associated with one of a series of candidate hypotheses to deliver healthcare to the patient; tracking a change in a quality of care metric directed to the patient with completion of a portion the protocol, the quality of metric including at least one of a time to rate of reduction in a health risk to the patient and a time to or rate of reduction in symptom or abnormal biometric data of the patient; and outputting an alert in response to the quality of care metric exceeding a threshold.

20 Claims, 4 Drawing Sheets

(56) References Cited

OTHER PUBLICATIONS

United States Patent and Trademark Office, "Notice of Allowance," issued in connection with U.S. Appl. No. 12/241,193, mailed on Feb. 1, 2012, 5 pages.

Institute of Medicine, "To Err Is Human: Building a Safer Health System," (Nov. 1999).

Kim Dixon, "U.S. Posts Hospitals Death Rates for Heart Ailments," http://news.yahoo.com/s/nm/20070622/wr_nm/hospital_mortality_dc_3;_ylt=AucC19F2jTf4Yfr5Q_gSHGUE1val (Jun. 21, 2007).

Judith Graham, "Patient Survival Data Now Public," http://www/chicagotribune.com/news/nationworld/chi-heartattacksjun22,1,4216626.story?track=rss (Jun. 22, 2007).

Bond, Raehl and Franke, "Medication Errors in United States Hospitals," http://www.medscape.com/viewarticle/409777_4, Pharmacotherapy vol. 21, Num. 9 (2001).

Agency for Healthcare Research and Quality, "Medical Errors: the Scope of the Problem," http://www.ahrq.gov/qual.errback.htm. (2000).

American Heart Association Rapid Journal Access Report, "Swift System for Heart Attack Care Improves Treatment, Cuts Costs," http://www.eurekalert.org/pub_releases/2007-06/aha-ssf061107.php (Jun. 11, 2007).

\* cited by examiner

SYSTEM AND METHOD TO MANAGE A QUALITY OF DELIVERY OF HEALTHCARE

CROSS-REFERENCE TO RELATED APPLICATIONS

The present application claims the benefit as a continuation of and priority to U.S. patent application Ser. No. 12/241,193, filed on Sep. 30, 2008, for "System and Method to Manage a Quality of Delivery of Healthcare," which is incorporated herein by reference in its entirety.

BACKGROUND

The subject herein generally relates to a system and method to manage a quality of delivery of healthcare to a patient, and more specifically, to automatically track reduction of health risk to the patient with progression through a protocol to treat the patient.

Hospitals and other medical facilities (e.g., imaging centers, cardiology treatment centers, emergency rooms, surgical suites, etc.) include various workflows to deliver diagnosis or treatment to admitted patients. These workflows are comprised of events that employ various resources, such as imaging rooms, physicians, nurses, radiologists, cardiologists, clinicians, technicians, etc.

Typically, delivery of medical care includes criticality to a time of delivery (such as to prevent irreversible damage or likelihood of mortality). For example, in the case of cardiac care, delivery of critical care with respect to a cardiac failure can have an estimated time criticality of less than 4 hours to prevent irreversible damage and patient mortality. As such, cardiac car remains a significant health care issue, where first diagnosis can happens in the emergency medical department. There are also numerous other critical medical conditions that similarly require urgent medical intervention within a significantly short period of time.

A certain known method of standard of care can be referred to as "evidence based medicine" that includes integrating individual clinical expertise with evidence based external best practices. However, at least one problem of the evidence based medicine technique can include how to integrate clinical expertise with evidence based external best practices in view of a growth rate of clinical knowledge that exceeds human ability to assimilate.

The above-mentioned problem can be addressed by the subject matter described herein in the following description.

BRIEF SUMMARY

The system and method of the subject matter described herein can be directed to manage a quality of delivery of medical care provided through a number of external and internal factors. The system and method can provide for the repeatable, reliable delivery of healthcare, as well as generally rapid, repeatable, reliable decision support to clinical staff that can reduce variance in a delivery of healthcare and thereby improve quality of healthcare delivery and provide a more structured process to diagnostic investigation.

According to one embodiment, a method to manage a quality of delivery of healthcare to a patient. The method comprises the steps of tracking completion of a portion of a protocol associated with one of a series of candidate hypotheses to deliver healthcare to the patient; tracking a change in a quality of care metric directed to the patient with completion of a portion the protocol, the quality of metric including at least one of a time to rate of reduction in a health risk to the patient and a time to or rate of reduction in symptom or abnormal biometric data of the patient; outputting an alert in response to the quality of care metric exceeding a threshold.

According to another embodiment, a system to manage delivery of healthcare to a patient. The system comprises a database having a series of templates, each template comprising at least one keyword associated with a medical condition and a protocol to diagnose or treat, and a controller with a memory in communication with a processor. The memory includes program instructions for execution by the processor to perform the steps of: tracking completion of a portion of a protocol of the template associated with one of a series of candidate hypotheses to deliver healthcare to the patient, tracking a change in a quality of care metric directed to the patient with completion of a portion the protocol, the quality of metric including at least one of a time to rate of reduction in a health risk to the patient and a time to or rate of reduction in symptom or abnormal biometric data of the patient, and outputting an alert in response to the quality of care metric exceeding a threshold.

Various other features, objects, and advantages of the invention will be made apparent to those skilled in the art from the accompanying drawings and detailed description thereof.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
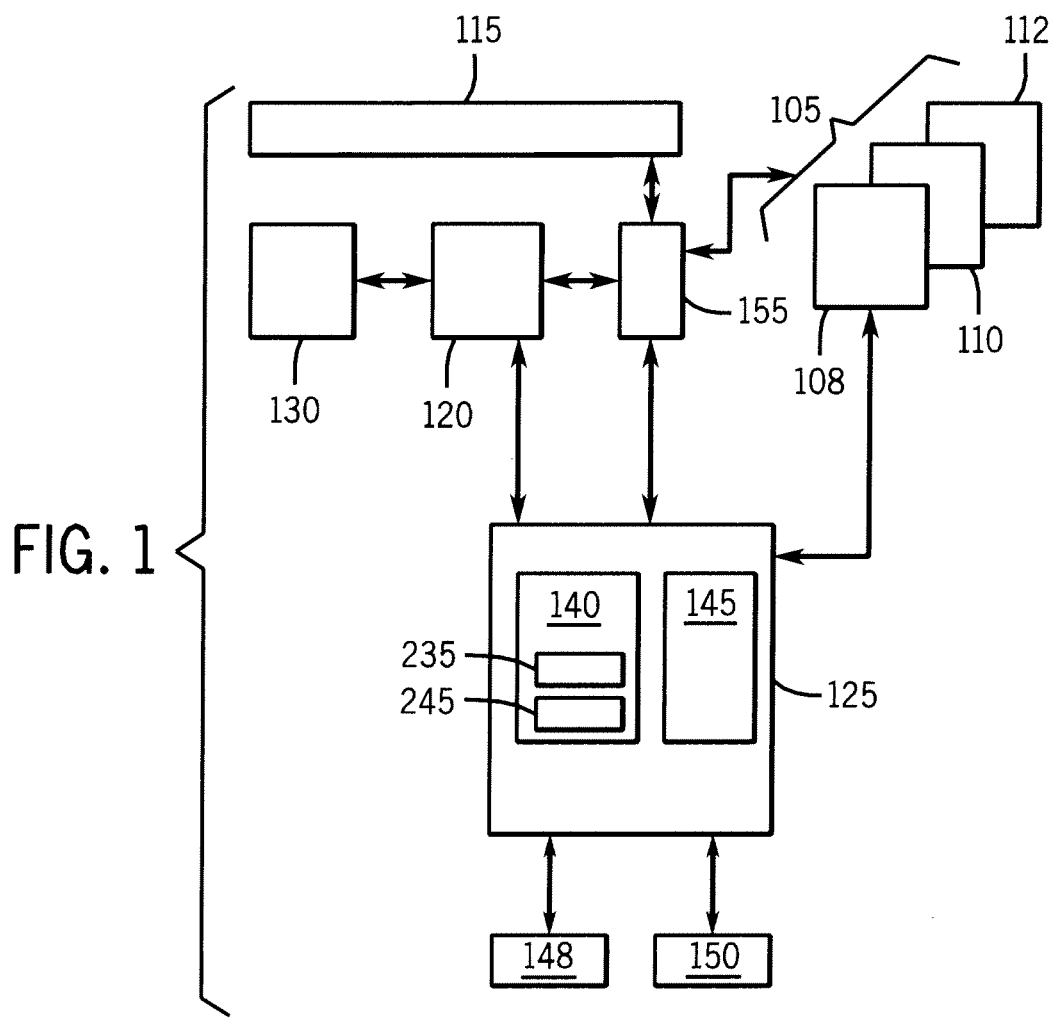
FIG. 1 is a diagrammatic overview of an embodiment of system to manage a workflow.

FIG. 1 illustrates a schematic diagram of an embodiment of a system 100 to manage resources 105 (e.g., physician or surgeon or other staff 108, medical equipment 110, laboratory systems 112, etc.) in the delivery of healthcare to patients 115. An embodiment of the system 100 includes agents 120 in communication (via wired or wireless connection) with a central server or controller 125.

An embodiment of the agent 120 generally includes computer-readable program instructions in or not in combination with one or more devices (e.g., clocks, timers, blood pressure monitors, electrocardiogram (ECG) monitors, temperature monitors, etc.) operable to track properties 130 (e.g., quality metrics such as wait time or biometric data such as blood pressure, pulse, respiration rate, laboratory results, etc.) associated with each patient 115. Each agent 120 can be generally operable to acquire data of the measured changes in the properties 130 associated with each of the patients 115. The agent 120 can be created upon introduction or admission of the patient 115 into the workflow. The agent 120 can be generally operable to communicate or collaborate in general real-time with one another, as well as with the patient 115. FIG. 1 shows the agent 120 located at the respective patient 115, respectively. Yet, it should be understood that one or more of the agents 120 or portions thereof can otherwise be located at the central server or controller 125.

One embodiment of the agent 120 can be configured to sense, detect, or track a presence and an awareness. Presence generally refers to an ability of the agent 120 to express or communicate a current state of activity (e.g., available, partially in-use, fully in use, etc.) of itself to other agent 120 in the system 100. Awareness generally refers to an ability of the agent 120 to sense the presence (as described above) of other agent 120 in the system 100. For example, awareness can include an ability of one agent 120 to track the activities of the agent 120 or patients 115 correlated thereto in the workflow. The combination of presence and awareness enables each agent 120 to initiate a communication or collaboration with one another to identify or calculate a length of time to get a response from one another. Awareness also allows the agent 120 initiating a communication or collaboration with other agents 120 to make decisions about mode of communication (e.g., route, wireless versus wired connection, etc.) to establish contact amongst multiple agents 120. An ability to express or communicate the presence and leverage the awareness allows the agent 120 to initiate communications or collaboration with one another and to respond to communications from other agents 120 associated with other patients 115.

An example of the agent 120 can receive/communicate patient data, receive/communicate requests for a work order and a report status, receive/communicate patient notifications to report for an event or step in the workflow (e.g., testing, imaging), receive/communicate problems, and receive/communicate orders for or results of tests. Examples of agent 120 can also operable to contact respective physicians waiting for critical patient information using an identified best mode of communication (e.g., beeper, home telephone, email, cellular phone, text message, etc.). Additionally, physicians 110 or patients 115 can communicate via computer messaging system s or other known type of input (e.g., keyboard, touch-screen, voice recognition, etc.) with the agent 120 in the workflow community to gain access to information and collaborate with agent 120 at any given point in time of the workflow.

The series of agents 120 can include, or the system 100 can further include, an additional agent having a general ability to supervise or track all of the resources 105 and patients 115 in the workflow, and identify or detect for errors (e.g., critical patient needs or wait time not being met in a timely manner). Agent 120 may also represent physicians, which may be especially useful when team medicine is required to administer care in complex treatment situations.

The agent 120 can be programmed with instructions of the protocol to direct the patient through the resources (e.g., medical equipment or space or personnel of the hospital diagnostic departments). The agent 120 can acquire or track data of various properties (e.g., consciousness, pulse, blood pressure, breathing rate, etc.) regarding the patient's medical condition and/or interact with the personnel to output the appropriate level of urgency of the patient 115 for viewing by the staff 108. The agent 120 can also be operable to re-factor or schedule a sequence of tests or resources, if availability of one procedure or respective resource occurs earlier than a predicted or forecast sequence or schedule of the procedure or availability of resources (unless there are medical reasons with respect to bio-markers etc, that drive such a need). The agent 120 can act as the patient's proxy when negotiating tests.

The agent 120 can update databases of template 210 on completion of any test, or any other instrumented data is taken. The agent 120 can also acquire or receive data from the various resources 105 (e.g., imaging system, PACS, physician, caregiver, staff, etc.) as institution manages the medical condition of the patient 115. The agent 120 can leverage an increased ability to gather information by the integration of patient care management with the system 100. The system 100 can be generally operable via the agent 120 to track the dynamics of individual or population of patients 115 over time and their respective needs and demands on resources 105.

An embodiment of the controller 125 is connected in communication with each of the agent 120. An embodiment of the controller 120 includes a memory or database 140 generally operable to receive updated values or measurements of tracked properties 130 on a continuous or periodic basis of the patient 115.

The controller 125 can also include a processor 145 generally configured to execute program instructions stored in the memory 140. Although the memory 140 and processor 145 are shown at the controller 125, it should be understood that the memory 140 or processor 145 can comprise remote portions at the agent 120 or other components of the system 100.

The controller 125 can also be in communication with an input device 148 and an output device 150. Examples of the input device 148 include a keyboard, an touch screen or graphic interface, mouse, toggle switches, etc. Examples of the output device 150 can include monitors, touch-screens or graphic interfaces, kiosks, dashboards, etc.

An embodiment of the system 100 can further a location sensing or location system 155 comprising sensing devices operable to track a location of each patient 115 or resources. An embodiment of the location system 155 is operable to communicate a location of each patient 115 relative to a predetermined reference. The location system 155 can be operable to track in coordinates, or by room or floor number, etc. The location system 155 can be in wireless communication with the controller 125. An embodiment of the location system 155 can employ electromagnetic technology, radio frequency (rF) technology, optical technology, global positioning system (GPS) technology or combination thereof or other position measuring or locating technology known in the art.

Figure 2:
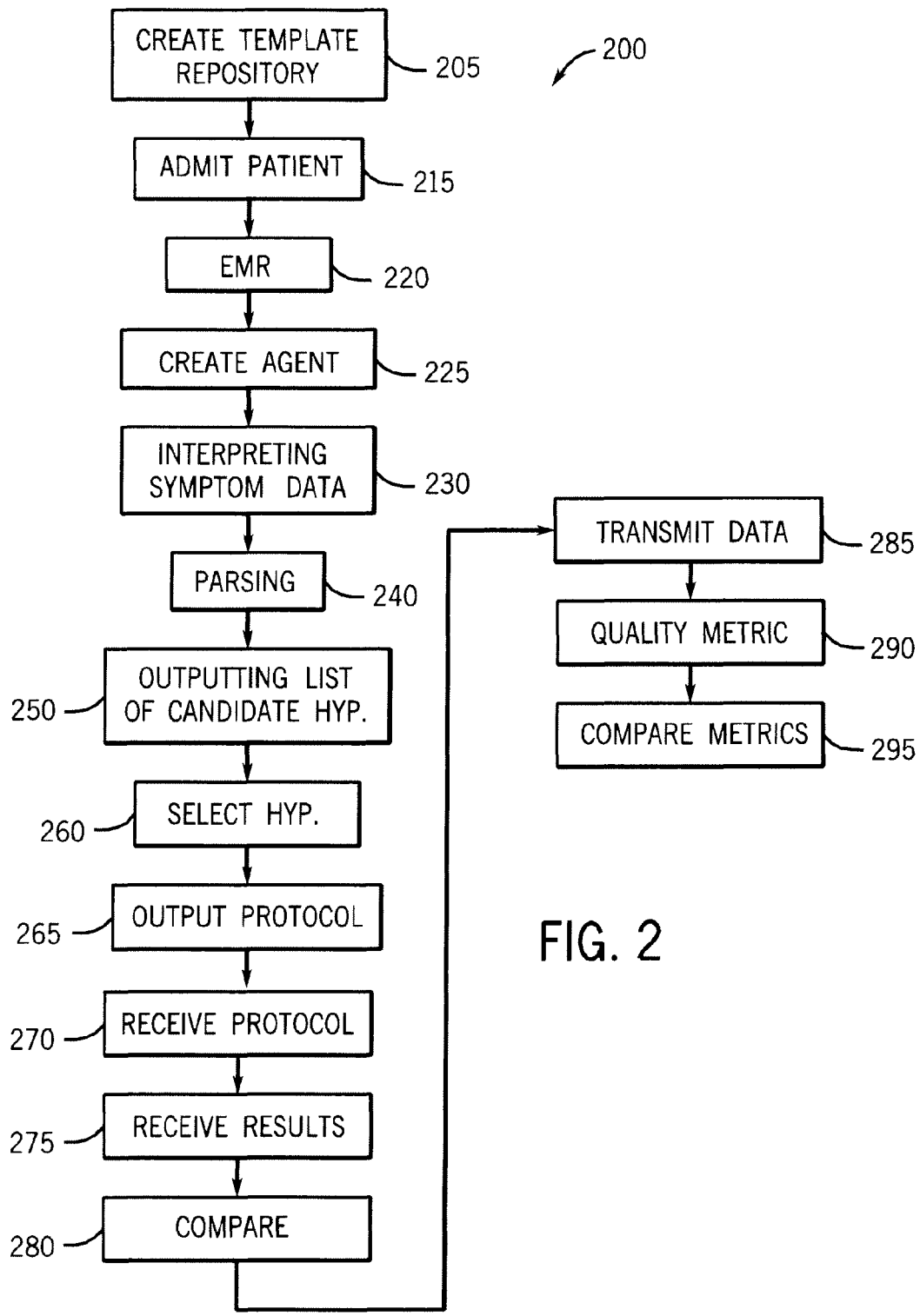
FIG. 2 is a flow diagram illustrating an embodiment of a method to manage the workflow with the system of FIG. 1.
Figure 3:
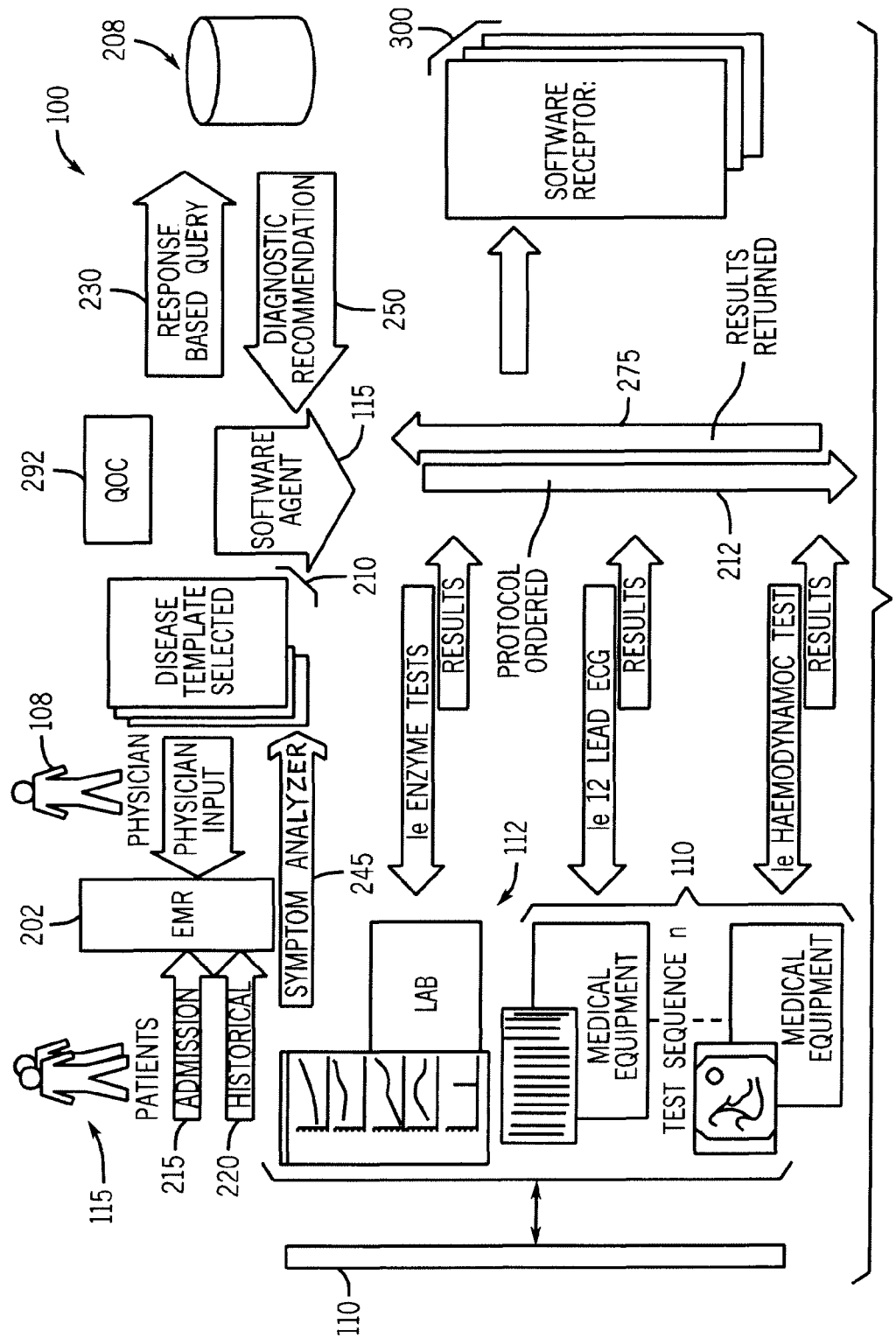
FIG. 3 is a schematic diagram illustrating an embodiment of operation of the system of FIG. 1 to manage delivery of healthcare to a patient.

FIGS. 2 and 3 include schematic diagrams to illustrate an embodiment of a method 200 of operation of the system 100 to manage (e.g., scheduling) a quality of delivery of healthcare to the patient(s) 115 through events of the workflow. It should also be understood that the sequence of the acts or steps of the method 200 as discussed in the foregoing description can vary. Also, it should be understood that the method 200 may not require each act or step in the foregoing description, or may include additional acts or steps not disclosed herein. It should also be understood that one or more of the steps of the method 200 can be represented as computer-readable program instructions for execution by one or more processors of the agent 120 or the controller 125.

Assume for sake of example that several conditions are possible for entry or admission of patient, including: a status of patient may be conscious, a patient may have medical history accessible through an Electronic Medical Record (EMR) 202, or a patient may be neither conscious or an EMR 202 of the patient may be inaccessible or may not exist. The system 100 and method 200 of the subject matter can accommodate each of the above-described scenarios. Also assume that admission can include a sequential assignment of a hospital admission number that uniquely identifies each patient 115.

Step 205 includes creating a repository or database of templates 210 each correlated to diagnosis of specific disease states or medical conditions. An embodiment of step 205 includes creating and storing the template 210 that comprises at least one symptom correlated to the disease state or medical condition. Step 205 can include creating instructions to initiate at least one medical diagnostic protocol (e.g., images to acquire, laboratory test to complete, etc.) 212, and storing or combining the instructions with the respective template 210.

The step 205 can further include communicating between the template 210 and a database 208 (e.g., national, or international or medical advisory repository of healthcare standards and protocol 212 and performance metrics). Examples of databases 208 can include an insurance provider database to provide a more uniform national performance model to compare healthcare provider institutions, protocols 212 authored locally at the institution, or provided by national organizations such as the AHA, ACC or other equivalent professional accredited institutions.

An embodiment of step 205 can further include storing a schedule of drug prescriptions or interaction within each template 210, or as a stand-alone template 210. For example, there may be cases where negative drug interaction states can compromise patient care, unintentionally or intentionally. The template 210 can include instructions to identify or detect negative drug interactions or output a change (e.g., increase) to health risk (described in more detail below) correlated to one or more drug interactions that can be stored or combined with the system. The instructions of the template 210 associated with negative drug interactions can also be represented as an automated protocol (e.g., communicate instructions to schedule or request a set of tests or procedures or acquisition of biometric data, instructions to execute an alert/alarm) 212 associated with increased health risk to the patient 115 caused by respective negative drug interaction.

Step 215 includes admitting the patient 115 to receive the delivery of healthcare. Step 215 can include obtaining or collecting at least one symptom data of each patient 115 that can be stored or combined with the template 210. An embodiment of the collecting step 215 can be performed throughout the admission's process, including collecting symptom data during transport of the patient 115 in an ambulance to the hospital, or from an emergency call, or from relatives/onlookers. The symptom data (e.g., consciousness, complaints, symptoms, etc.) can be entered in response to questions illustrated on an interface, or free flow discussion with a healthcare provider.

Step 220 includes acquiring or creating the EMR 202 directed to the patient 115. The acquired symptom data can be combined with newly created EMR 202 or with the historical data stored in a historical EMR 202 directed to the patient 115. Step 225 includes creating the agent 120 unique to the patient 115, the agent 120 as described in the above-description of the construction of the system 100.

Step 230 includes interpreting or parsing at least the symptom data in addition to all or portion of other historical or biometric data of the EMR 202, and transmitting or communicating an extraction of this data to a module of program instructions herein referred to as the decision engine 235. An embodiment of step 230 includes the agent 120 interpreting the symptom data and other acquired data as entered into the EMR 202 of the patient 115, extracting the data from the EMR 202 relative to symptom or other acquired data in the EMR 202, and integrating the extracted data with a unique identifier for communication to the decision engine 235.

Step 240 includes interpreting or parsing the repository of templates 210 in view of or for comparing to the acquired symptom data. An embodiment of the decision engine 235 can parse the collected symptom data for key words or symptom measurements or test result ranges via a module of program instructions herein referred to as the symptom analyzer 245. An embodiment of the symptom analyzer 245 can also be integrated at the controller 125 or at the agent 120.

Step 250 includes generating or acquiring a series or list of hypotheses 252 of the potential medical condition of the patient 115 for illustration to the healthcare provider (e.g., physician 108, etc.). An embodiment of the hypotheses 252 can include a portion or more of the data stored in the disease templates 210. Another embodiment of the system 100 may facilitate a decision or identification in accordance to a ranking of confidence 253 in multiple hypotheses 252. Based on available data, multiple hypotheses 252 can be ranked from most likely to least likely, greatest to least confidence or confidence level 253, or vice versa, or combinations thereof.

Step 250 can further include calculating the risk factor, probability, or confidence 253 (e.g., probability or likelihood that one in the list of hypotheses 252 is correct diagnosis and/or treatment in delivery of healthcare to the patient) of each hypothesis 252 relative to another. One embodiment of the confidence level 253 can include a percentage match of parsed terms from the patient EMR 202 that match keywords associated with the template 210, or predetermined confidence levels 253 associated with prior medical history of patient associated with a particular medical condition associated with template 210, or confidence level 253 associated with genetic risk factor of the patient to medical condition associated with template 210.

For example, a single symptom data representative or indicative of chest pain can suggest the series of hypotheses 252 to include a case of indigestion. A combination of symptom data that includes symptom data representative or indicative of chest pain accompanied with symptom data representative or indicative of constricted breathing can suggest the series of hypotheses 252 to include a case of an allergic response, or the series of hypothesis 252 to include a case of an evolving cardiac condition. The healthcare provider or physician 108 can scroll or scan through the list of hypotheses 252 output by the system 100 or method 200. The system 100 or method 200 can also include output of indicators or instructions of possible diagnostic sequences or protocols 212 associated with each hypotheses 252 for approval or designation by the physician or caregiver 108. The system 100 or method 200 can also include outputting the risk factor or confidence 253 for each hypotheses 252 for viewing and consideration by the physician. One or more of the above-described steps can be repeated from admission through to discharge of the patient 115.

Step 260 includes receiving an instruction of a selection of a candidate 262 from the series of hypotheses 252 for implementation. One embodiment of the system 100 may make a decision or selection of a candidate 262 from the list of hypotheses 252 according to the confidence 253 in the candidate 262 relative to the other hypotheses 252. Step 265 can include automatically outputting a protocol 212 of steps or schedule of tasks (e.g., acquire diagnostic image, electrocardiogram (ECG), stress test, etc.) to complete in response to the instruction of the selection of candidate hypothesis 262. Step 265 can include automatically initiating and outputting a schedule of the resources 105 (e.g., imaging system, physician, staff, etc.) to complete the protocol 212 automatically in response to the instruction of the selection of the candidate hypothesis 262. Assume that the template 210 associated with the candidate hypothesis 262 includes the instructions or steps and respective resources 105 to complete the protocol 212 on the patient 115.

Step 270 includes communicating the steps of the protocol 212 to or receiving the steps of the protocol 212 at the agent 120. Step 275 can include receiving the test results or completion of one or more of the steps or protocol 212 at the agent 120. Step 280 includes comparing the completion of steps or protocol 212 relative to the schedule of steps or test or protocol 212 to complete according to the template 210. Step 285 includes transmitting the test results or data of completion of executed steps of the protocol 212 to the Symptom analyzer 245 or receiving the test results or data of completion of executed steps of the protocol 212 at the symptom analyzer 245.

An embodiment of the system 100 and method 200 can automatically acquire and update output of data of changes to the recommended protocol (e.g., sequence of one or more diagnostic tests or image acquisition) 212 associated with the selection of the candidate hypothesis 262.

Step 290 includes interacting or communicating between one or more of the agent 120, one or more the resources 105, the template 210, and the symptom analyzer 245 to track progress of a quality of care metrics 292 (See FIG. 3) directed to delivery of healthcare to the patient 115. An embodiment of the parameters and thresholds of the quality of care metrics 292 can be listed or stored with the disease template 210 or independent thereof. Step 290 can be performed periodically or continuously through or during a portion or all of the protocol associated with the first selection of the candidate hypothesis 262. One embodiment of the quality of care metrics 292 include, but are not limited to, tracking relationship of delivery of the portion or all of the protocol to time to or rate of mitigation or reduction of the health risk to the patient, time to or rate of reduction in symptoms of patient, or time to rate of reduction in abnormal biometric data of patient, or combination thereof.

Examples of quality of care metrics directed to health risk to the patient can be quantified by tracking or acquiring input of at least one of the following: Acute Physiology and Chronic Health Evaluation (APACHE II) as a measure of how likely to make it out of intensive care unit; Simplified Acute Physiology (SAP) score; Glasgow Coma Score (GCS) as an assessment of consciousness; Sequential Organ Failure Assessment (SOFA) score as an assessment of person's organ function or rate of failure; Apgar Assessment of a newborn's adjustment to life; Pain perception profile; visual analogue scale (VAS); quality of life metrics such as EDLQ, SF36; depression scale such as CES-D; impact of event scale (IES); or thrombosis risk assessment, or trend therein, or combination of above. Of course, the above list of quality of care metrics directed to health risk to the patient is not limiting, and other miscellaneous scores and assessments known in the medical field can be used.

For example, the system 100 can track progress of the quality of care metric 292 via tracking time to or rate of mitigation or reduction of health risk associated with or time to or rate of reduction of abnormal symptom or biometric tracking data of the patient 115 such as chest pain, abnormal heart rate or pressure; respiratory rate or pressure; temperature; blood test parameters such as oxygen level, glucose level, iron level, white blood cell count, red blood cell count, platelets level, hemoglobin level, cholesterol level, lipoprotein level, troponin level, enzyme levels, electrolyte levels, calcium levels, BUN levels, CRP levels, homocysteine levels, etc.

For example, in response to calculating or detecting or acquiring data that the protocol 212 of the first selection of the candidate hypothesis 262 does not cause a threshold mitigation or reduction of the symptom (e.g., abnormal biometric tracking data, pain, etc.) or health risk to the patient within a threshold time or at a threshold rate of reduction, the system 100 may re-calculate or lower the confidence 253 in the first candidate hypothesis 262 and respectively raise the confidence in one or more of the remaining hypotheses 252 in the list. The remaining list of hypotheses 252 for a symptom of chest pain can be associated with the gall bladder, or even spastic-colon (which has symptoms that can be construed as cardiac in nature).

Step 290 can include acquiring or receiving additional quality of care metrics 292 at the agent 120 for communication to the output device (e.g., dashboard, workstation, kiosk, etc.) for viewing as the respective patient 115 moves through from admission to discharge from the institution. Examples of additional metrics 292 can include wait time for the resource 105 (e.g., wait time for admission to a medical/surgical bed, wait time between admission relative to preliminary diagnosis, etc.), and percent compliance to protocol of template.

Step 295 includes comparing and reporting the tracking of quality of care metric 292 relative to a threshold. The metrics 292 may be reported to departmental or institutional management or individual physicians or caregivers for quality feedback. The decision engine 235 or other portion of the system can compare the acquired measurement of the metrics 292 relative to a threshold, and if at least one measured metric 292 falls outside the threshold range (e.g., exceeds threshold) can cause or trigger a reallocation or scheduling of resources 105. In response to acquiring or measuring the at least one metric 292 falling outside the threshold range, the system 100 can also generate a request for a re-calculation or identification of hypotheses 252, or create a re-calculation of confidence 253 in one candidate hypothesis 262 relative to other hypotheses 252 (e.g., decreasing confidence 253 in selected candidate hypothesis 262 in proportion to increasing confidence 253 in one or more other hypotheses 252). One embodiment of the decision engine 235 or other portion of the system 100 can compare the quality of care metrics 292 relative to thresholds times or rates of reduction directed to trigger or cause an alert mechanism to inform the physician or caregivers 108 of delivery of care delivered to the patient 115 below a threshold (e.g., time to or rate of reduction of symptom, time to or rate of reduction of health risk, etc.).

In response to updating and comparing the health risk directed to one patient 115 in response to tracking changes in comparison to thresholds of step 295, changes to biometric data, changes to wait times, etc., step 298 can include changing the priority of the protocol 212, including tests or procedures or scheduling of resources 105 (e.g., physicians, surgeons, staff, surgery or other procedural or examination rooms, equipment such as imaging systems, etc.) relative to scheduling of resources 105 directed to other patients 115. For example, suppose the candidate hypothesis 262 was that a first patient is not cardiac. Later in the process this is proved incorrect, the patient 115 may now become highly urgent for cath-lab admission for vessel opening. In response to a change to the highly urgent status, the symptom analyzer 245 can automatically increase value of risk associated with the patient 115 to be greater than the risk value or model of all other non-urgent patients 115, or relative to the risk value or model of non-urgent patients waiting for surgery, and accordingly change the scheduling of resources 105 such that that urgent patient 115 can be schedule to receive the protocol 212 (e.g., a test or a procedure) before other non-urgent patients 115.

The above-described steps of the method 200 can include series of reiterations that includes re-analysis, output, selection, and execution of protocol associated with the list of candidate hypothesis correlated to various templates 210, and yet maintain viewing and comparison to the remaining unselected candidate hypotheses and respective templates 210. Refer again to the example of the symptom of chest pain as described above.

The system 100 can also include one or more software receptors 300. An embodiment of the software receptor 300 monitors data flows across a series of patients or a patient population, and passively track/observe and pass data to the system 100 in tracking delivery of quality of care, infection management, and disease population state monitoring (i.e. looking for early indicators of potential disease outbreaks).

As the system 100 acquires data, the system 100 can detect or identify anomalies in the acquired test results or medical condition relative to the selection of the candidate hypothesis of the patient 115. In response to detection of an anomaly or change in a biometric parameter of the patient 115, the system 100 can automatically convert or output the test results or medical condition associated with the anomaly into a query to the decision engine 235. In response to the query, the decision engine 235 can automatically parse the database of templates 210 and output or generate a revised list of hypotheses 252.

The system 100 can further output an alert in response to detection or acquiring data indicative of a contra-indicator (e.g., actions that may increase health risk to patient) via the symptom analyzer 245 such that the physician can be alerted to errors of interpretation, null of selection of candidate hypothesis, and potential alternate candidate hypotheses. Thereby, a technical effect of the system 100 can include the ability to continually aid the physician with medical knowledge applied uniquely to the situation or medical condition of the patient at hand. The system 100 and method 200 can also enhance delivery of healthcare to patients 115 convolved with multi-disease states. The medical condition of patients (e.g., older patients or chronically ill patients) can go unstable, or new failure mode can develop.

The template 210 can be modified to accommodate the interaction with various bodies of knowledge, including data of experiences in similar cases, or data of cases with some equivalence may be shared. The system 100 may output diagnostic protocols 212 that are significantly different or enhanced relative to different stages of disease states of the patient. The system 100 can also acquire or receive clinical best practices and add to the protocol of various template 210s as appropriate. In this fashion, the integration of new knowledge with the clinical practitioner can occur on an "as-needed" basis.

The following is a description of management of quality of delivery of healthcare to a patient at a long-term care facility via the system described above. The system 100 can acquire the protocol 212 of a plan of a quality of care metrics 292 to address needs and risks for each patient, and arrange protocol 212 of the plan of the quality of care metrics 292 in a template 210 associated with various conditions for delivery of healthcare at the long-term care facility. At a long-term care facility, the protocol 212 for the delivery of healthcare may involve lesser need or no need for diagnostic tests or procedures.

The agent 120 can receive data representative of the quality of care metric 292 and relay to the software receptor 300. The software receptor 300 can forward the data to the EMR 202 according to Institutional policy. The system 100 can acquire or receive quality of care metrics 292 to combine with other data (e.g., historical data of an EMR 202, current data acquired at the software receptor 300, and threshold criteria of quality of care metrics 292) so as to calculate or output the general real-time values or measure of quality of care metrics 292 delivered to the particular patient 115 relative to the threshold (e.g., to trigger an alarm).

For example, in a case of a comatose medical condition, the plan of care protocol 212 as stored in a template 210 may include the quality of care metric 292 that the patient 115 be turned at a threshold time interval. If the agent 120 associated with the patient 115 acquires or measures the quality of care metric 292 (e.g., time data via clock) that detects that no movement of the patient 115 has occurred beyond threshold time interval, the agent 120 can cause communication of a signal to trigger an alarm at the output device 150. The system 100 can also output changes in alarm conditions associated with changes in acquired thresholds in quality of care metrics 292 described above. The system 100 can also track changes in quality of care metrics 292 for output in reports to benefit providers (long term care insurance), legal guardians, or family members. The subject matter described herein provides a process to enhance performance of long term care organizations, and may help with accreditation and comparison of care facilities.

Figure 4:
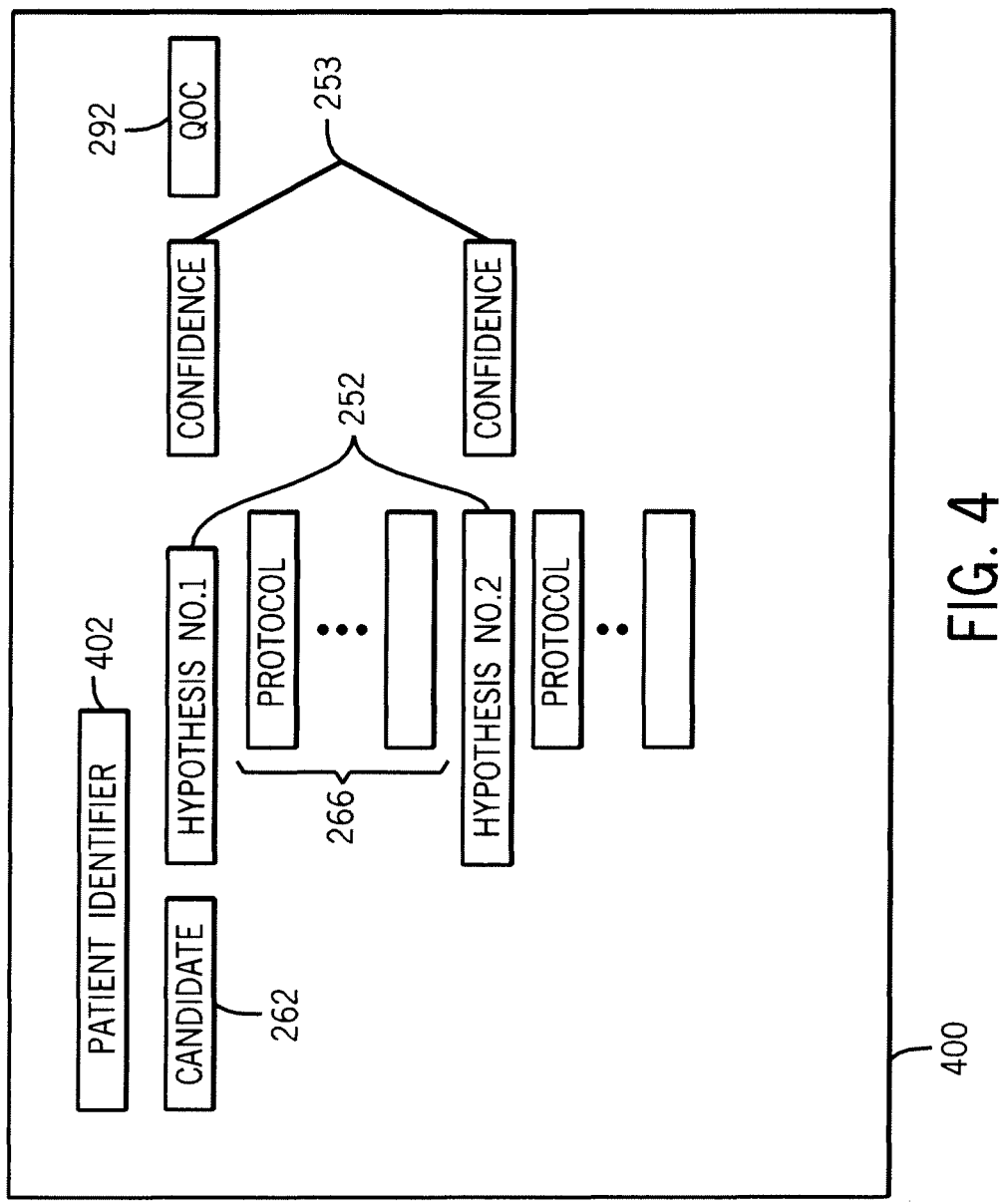
FIG. 4 is a schematic diagram of a dashboard comprising output of the system of FIG. 1.

FIG. 4 illustrates an embodiment of a dashboard 400 illustrative to the output from the system 100. The dashboard 400 includes an illustration of the patient identifier 402, the list of hypotheses 252, the selection of the candidate hypothesis 262, the list of protocol or instruction associated with each hypotheses 252, the confidence 253 in each hypotheses, and the one or more quality of care metrics 292 tracked by the system 100. The quality of care metrics 292 may be directed to all patients 115 or individually to each patient 115.

A technical effect of the above-described system 100 and method 200 includes enhancement of management of quality of delivery of healthcare in a workflow in general real-time. The system 100 and method 200 can generally acquire the flow of information or acquired data from the various components of the system 100 or resources 105 and combine or arrange in a manner to aid the physician in decision-making and direct or steer the diagnostic investigation of the patient 115. Conformance to accepted methods and protocols 212 can aid timely execution, and potentially minimize mistakes or misses through continuity of decision making with respect to a specific patient.

Another technical of the system 100 and method 200 is to provide a means to monitor quality of care delivered to the patient 115 in general real-time, a means to automatically incorporate patient telemetry into care delivery, a means to monitor trends in quality of care delivery, and a means to enhance compliance with changes in care delivery. Another technical effect of the system 100 and method 200 includes reducing information overload to Caregivers by providing high value knowledge at the point of care in general real-time.

Although the systems 100 and methods 200 are described with respect to specific healthcare environment, systems 100 and methods 200 can be extended to any nature or type of workflow. Other examples include diagnostic equipment that supports multiple test types reconfigures self to support high priority customer need. Alternatively, a department schedule can have one operational profile one day or even one hour to suit a demand, and be reprogrammed with another operational schedule to suit a different demand in time. The system 100 and method 200 are also operable to create a schedule that accommodates combination or permutations of conditions. Thereby, the system 100 and method 200 afford flexibility and control of a workflow relative to those managed as only a linear function.

Although the subject matter is described herein with reference to medical diagnostic or cardiac treatment applications, it should be noted that the subject matter is not limited to this or any particular application or environment or environment (e.g., industrial, commercial, etc.).

This written description uses examples to disclose the subject matter, including the best mode, and also to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of managing a quality of delivery of healthcare to a patient, the method comprising:
   parsing, using a processor, a medical record for a patient, to identify at least one symptom data to compare to at least one keyword in each of a plurality of templates, the at least one keyword associated with a medical condition and a protocol to diagnose or treat the medical condition, each protocol comprising a plurality of tasks to be executed to complete the protocol according to a schedule associated with the protocol;
   outputting, using the processor, a) a plurality of candidate hypothesis each associated with a different templates and b) a confidence level associated with each candidate hypothesis;
   automatically outputting, using the processor, the protocol associated with a selected candidate hypothesis, the outputting to provide a representation of the protocol via an output device;
   tracking completion of a portion of the protocol associated with the selected candidate hypotheses to deliver healthcare to the patient, wherein tracking completion of the portion of the protocol includes tracking completion of tasks executed according to the schedule associated with the protocol;
   tracking a change in a quality of care metric directed to the patient with completion of the portion the protocol, the quality of care metric including at least one of a) a time to rate of reduction in a health risk to the patient and b) a time to or rate of reduction in symptom or abnormal biometric data of the patient;
   outputting an alert using the processor in response to the quality of care metric exceeding a threshold; and
   decreasing confidence in the selected candidate hypothesis and increasing confidence in one or more of the other plurality of candidate hypotheses triggered by acquiring the at least one quality of care metric exceeding the threshold.

2. The method of claim 1, further comprising: outputting via the output device an illustration of the at least one quality of care metric relative to the threshold and the completion of the portion of the protocol.

3. The method of claim 1, further comprising: increasing a priority of the patient relative to other patients in the schedule of resources if the at least one quality of care metric that exceeds the threshold such that the system schedules the patient to receive use of the resources before the other patients.

4. The method of claim 1, further comprising: generating a request for a re-calculation of a list of candidate hypotheses triggered by acquiring the at least one quality of care metric exceeding the threshold.

5. The method of claim 1, wherein the health risk to the patient includes at least one of mortality risk; acute physiology and chronic health evaluation (APACHE II); simplified acute physiology (SAP) score; Glasgow coma score (GCS); sequential organ failure assessment (SOFA) score; Apgar assessment; pain perception profile; visual analogue scale (VAS); quality of life metrics; depression scale; impact of event scale (IES); and thrombosis risk assessment.

6. The method of claim 1, wherein symptom or biometric data of the patient includes one or more of the following: a chest pain, an abnormal heart rate or pressure; a respiratory rate or pressure; a temperature; and a blood test parameters such as oxygen level, glucose level, iron level, white blood cell count, red blood cell count, platelet level, hemoglobin level, cholesterol level, lipoprotein level, troponin level, enzyme level, electrolyte level, calcium level, BUN level, CRP level, and homocysteine level.

7. A system to manage delivery of healthcare to a patient, the system comprising:
   a controller with a memory in communication with a processor, the memory including program instructions for execution by the processor to:
   parse a medical record for a patient, to identify at least one symptom data to compare to at least one keyword in each of a plurality of templates, the at least one keyword associated with a medical condition and a protocol to diagnose or treat the medical condition, each protocol comprising a plurality of tasks to be executed to complete the protocol according to a schedule associated with the protocol;
   output a) a plurality of candidate hypothesis each associated with a different templates and b) a confidence level associated with each candidate hypothesis;
   automatically output the protocol associated with a selected candidate hypothesis, the outputting to provide a representation of the protocol via an output device;
   track completion of a portion of the protocol associated with the selected candidate hypotheses to deliver healthcare to the patient, wherein tracking completion of the portion of the protocol includes tracking completion of tasks executed according to the schedule associated with the protocol;
   track a change in a quality of care metric directed to the patient with completion of the portion the protocol, the quality of care metric including at least one of a) a time to rate of reduction in a health risk to the patient and b) a time to or rate of reduction in symptom or abnormal biometric data of the patient;
   output an alert in response to the quality of care metric exceeding a threshold; and decrease confidence in the selected candidate hypothesis and increasing confidence in one or more of the other plurality of candidate hypotheses triggered by acquiring the at least one quality of care metric exceeding the threshold.

8. The system of claim 7, the controller further operable to: decrease confidence in the selected candidate hypothesis and increasing confidence in one or more of the other plurality of candidate hypotheses triggered by acquiring the at least one quality of care metric exceeding the threshold.

9. The system of claim 7, the controller further operable to: output to an output device an illustration of the at least one quality of care metric relative to the threshold and the completion of the portion of the protocol.

10. The system of claim 7, the controller further operable to: increase a priority of the patient relative to other patients in the schedule of resources if the at least one quality of care metric that exceeds the threshold such that the system schedules the patient to receive use of the resources before the other patients.

11. The system of claim 7, the controller further operable to: generate a request for a re-calculation of a list of candidate hypotheses triggered by acquiring the at least one quality of care metric exceeding the threshold.

12. The system of claim 7, wherein the health risk to the patient includes at least one of mortality risk; acute physiology and chronic health evaluation (APACHE II); simplified acute physiology (SAP) score; Glasgow coma score (GCS); sequential organ failure assessment (SOFA) score; Apgar assessment; pain perception profile; visual analogue scale (VAS); quality of life metrics; depression scale; impact of event scale (IES); and thrombosis risk assessment.

13. The system of claim 7, further comprising an agent to acquire the symptom or biometric data for communication to the controller, the symptom or biometric data of the patient comprising at least one of the following: a chest pain; an abnormal heart rate or pressure; a respiratory rate or pressure; a temperature; and a blood test parameters such as oxygen level, glucose level, iron level, white blood cell count, red blood cell count, platelet level, hemoglobin level, cholesterol level, lipoprotein level, troponin level, enzyme level, electrolyte level, calcium level, BUN level, CRP level, and homocysteine level.

14. The system of claim 7, wherein the quality of care metric includes a time since last turnover of the patient relative to a threshold.

15. The system of claim 8, wherein the confidence includes a percentage of terms in the medical record that match the keyword in each of the plurality of templates.

16. A non-transitory computer-readable storage medium including a set of instructions to be executed by a processor, the set of instructions, when executed, to implement a method of managing a quality of delivery of healthcare to a patient, the method comprising:

parsing a medical record for a patient, to identify at least one symptom data to compare to at least one keyword in each of a plurality of templates, the at least one keyword associated with a medical condition and a protocol to diagnose or treat the medical condition, each protocol comprising a plurality of tasks to be executed to complete the protocol according to a schedule associated with the protocol;

outputting a) a plurality of candidate hypothesis each associated with a different templates and b) a confidence level associated with each candidate hypothesis;

automatically outputting the protocol associated with a selected candidate hypothesis, the outputting to provide a representation of the protocol via an output device;

tracking completion of a portion of the protocol associated with the selected candidate hypotheses to deliver healthcare to the patient, wherein tracking completion of the portion of the protocol includes tracking completion of tasks executed according to the schedule associated with the protocol;

tracking a change in a quality of care metric directed to the patient with completion of the portion the protocol, the quality of care metric including at least one of a) a time to rate of reduction in a health risk to the patient and b) a time to or rate of reduction in symptom or abnormal biometric data of the patient;

outputting an alert in response to the quality of care metric exceeding a threshold; and decreasing confidence in the selected candidate hypothesis and increasing confidence in one or more of the other plurality of candidate hypotheses triggered by acquiring the at least one quality of care metric exceeding the threshold.

17. The computer-readable storage medium of claim 16, wherein the method further comprises: outputting via the output device an illustration of the at least one quality of care metric relative to the threshold and the completion of the portion of the protocol.

18. The computer-readable storage medium of claim 16, wherein the method further comprises: increasing a priority of the patient relative to other patients in the schedule of resources if the at least one quality of care metric that exceeds the threshold such that the system schedules the patient to receive use of the resources before the other patients.

19. The computer-readable storage medium of claim 16, wherein the method further comprises: generating a request for a re-calculation of a list of candidate hypotheses triggered by acquiring the at least one quality of care metric exceeding the threshold.

20. The computer-readable storage medium of claim 16, wherein symptom or biometric data of the patient includes one or more of the following: a chest pain, an abnormal heart rate or pressure; a respiratory rate or pressure; a temperature; and a blood test parameters such as oxygen level, glucose level, iron level, white blood cell count, red blood cell count, platelet level, hemoglobin level, cholesterol level, lipoprotein level, troponin level, enzyme level, electrolyte level, calcium level, BUN level, CRP level, and homocysteine level.

* * * * *